(12) United States Patent
Baranowitz

(10) Patent No.: US 8,575,128 B2
(45) Date of Patent: Nov. 5, 2013

(54) METHODS FOR TRANSDIFFERENTIATION OF BODY TISSUES

(76) Inventor: Steven Baranowitz, Wyncote, PA (US)

(*) Notice: Subject to any disclaimer, the term of this patent is extended or adjusted under 35 U.S.C. 154(b) by 0 days.

(21) Appl. No.: 13/413,411

(22) Filed: Mar. 6, 2012

(65) Prior Publication Data

US 2012/0196826 A1 Aug. 2, 2012

Related U.S. Application Data

(60) Continuation of application No. 13/023,152, filed on Feb. 8, 2011, now abandoned, which is a continuation of application No. 12/775,609, filed on May 7, 2010, now abandoned, which is a continuation of application No. 11/557,772, filed on Nov. 8, 2006, now abandoned, which is a continuation of application No. 10/600,745, filed on Jun. 19, 2003, now Pat. No. 7,176,189, which is a division of application No. 09/856,881, filed as application No. PCT/US00/21015 on Jul. 31, 2000, now Pat. No. 6,670,397.

(60) Provisional application No. 60/146,272, filed on Jul. 29, 1999, provisional application No. 60/168,558, filed on Dec. 2, 1999.

(51) Int. Cl.
*A61K 31/167* (2006.01)
*C07H 19/167* (2006.01)
*A61K 31/706* (2006.01)

(52) U.S. Cl.
CPC ............ *A61K 31/706* (2013.01); *C07H 19/167* (2013.01)
USPC ........................................ 514/48; 536/27.81

(58) Field of Classification Search
None
See application file for complete search history.

(56) References Cited

U.S. PATENT DOCUMENTS

| 6,054,441 | A | * | 4/2000 | von Borstel et al. ............. 514/45 |
| 6,087,168 | A | | 7/2000 | Levesque et al. |
| 6,255,291 | B1 | | 7/2001 | Germano |
| 6,670,397 | B1 | * | 12/2003 | Baranowitz ................... 514/568 |
| 7,176,189 | B2 | * | 2/2007 | Baranowitz ................... 514/45 |

FOREIGN PATENT DOCUMENTS

WO    WO94/21231    9/1994

OTHER PUBLICATIONS

Ohyanagi et al., "Effects of nucleotides and nucleosides on cell growth in vitro and in vivo" Acta Medica Kinki University (1995) vol. 20 No. 1 pp. 27-39.*
Brown et al., "Studies of the neuronal transdifferentiation process in cultured human pheochromocytoma cells: Effects of steroids with differing functional groups on catecholamine content and cell morphology," *Steroids*, vol. 63, pp. 587-594 (1998).
Dutt et al., "Transdifferentiation of Adult Human Pigment Epithelium into Retinal Cells by Transfection with an Activated H-ras Proto-Oncogene," *DNA and Cell Biology*, vol. 12, No. 8, pp. 667-673 (1993).
Ortiz et al., 'Induction of the Stellate Configuration in cultured Iris Epithelial Cells by Adenosine and Compounds Related to Adenosine 3':5'-Cyclic Monophosphate, *Proc. Nat. Acad. Sci.*, vol. 70, No. 8, pp. 2286-2290 (1973).
Noji et al., "Retinoic Acid Induces Polarizing Activity But is Unlikely to be a Morphogen in the Chick Limb Bud," *Nature*, vol. 350, pp. 83-86 (1991).
Tabin et al., "Retinoids Homeoboxes and Growth Factors: Toward Molecular Models for Limb Development," *Cell*, vol. 66, pp. 199-217 (1991).
Wanek et al., "Conversion by Retinoic Acid of Anterior Cells into ZPA Cells in the Chick Wing Bud." *Nature*, vol. 350 pp. 81-83 (1991).
Bittrich et al., "NO2-induced DNA Single Strand Breaks are inhibited by Antioxidative Vitamins in V79 Cells," *Chem. Biol. Interactions*, vol. 86, pp. 199-211 1993.
Itoh et al., "Effect of Natural β-Carotene on Oxidative Stress of Vascular Endothelial Cells," *Vitamins*(Japan), vol. 71, No. 8, pp. 357-363 (1997).
Ju et al., "Pattern Duplication by Retinoic Acid Treatment in the Regenerating Limbs of Korean Salamander Larvae, *Hynobius leechii*, Correlates Well With the Extent of Dedifferentiation," *Developmental Dynamics*, vol. 199, pp. 253-27 (1994).
Sherman et al., "Basic Fibroblast Growth Factor (bFGF) Acts Intracellularly to Cause the Transdifferentiation of Avian Neural Crest-Derived Schwann Cell Precursors into Melanocytes." *Development*, vol. 118, pp. 1313-1326 (1993).
Baer et al., "Transdifferentialtion of Distal but not Proximal Tubular Epithelial Cells from Human Kidney in Culture," *Experimental Nephrology*, vol. 7, pp. 306-313 (1999).
Henderson et al., "Inhibition of Animal and Invertebrate Cell Growth by Naturally Occurring Purine Bases and Ribonucleosides," *Pharm. Ther.*, vol. 8, pp. 539-571, (1980).
Giotta et al., "Guanosine 5'-Thlphosphate Inhibits Growth and Stimulates Differentiated Functions in B16 Melanoma Cells," *Experimental Cell Research*, vol. 112, pp. 385-393 (1978).
Bynum, "Characterization of Adenosine-Induced Cytostasis in Melanoma Cells," *Cancer Research*, vol. 40, pp. 2147-2152 (1980).
Osti et al, "Human Leukemia K562 Cells: Induction to Erythroold Differentiation by Guanine, Guanosine and Guanine Nucleotides," *Haematologica*, vol. 82, pp. 395-401 (1997).
Reginelli et al., "Digit tip regeneration correlated with region of Msx1 (Hox7) expression in fetal and newborn mice," *Development* (Cambridge), vol. 121, No. 4, pp. 1065-1076 (1995).
Menke et al., "Transforming growth factor-beta-induced upregulation of transforming growth factor-beta receptor expression in pancreatic regeneration," *biochimica et biophysica Acta. Molecular Cell Research*, Elsevier Science Publishers, Amsterdam, NL, vol. 1449, No. 2, pp. 178-185 (1999).
Rao et al., "Hepatic transdifferentiation in the pancreas," *Seminars in Cell Biology*, vol. 6, No. 3, pp. 151-156 (1995).
Baranowitz, "Regeneration Neural Crest Derivatives and Retinoids a New Synthesis," *Journal of Theoretical Biology*, vol. 140, No. 2, pp. 231-242 (1989).

(Continued)

*Primary Examiner* — Eric S Olson
(74) *Attorney, Agent, or Firm* — Troutman Sanders LLP

(57) ABSTRACT

The invention relates to methods for transdifferentiation of body tissues which can be used to generate specific cell types needed for regenerating organs or body parts, following cellular degeneration, injury or amputation. The present invention also describes the use of tissue transdifferentiation for treating cancer and autoimmune disease.

10 Claims, 2 Drawing Sheets

(56) References Cited

OTHER PUBLICATIONS

Database CA 'Online! Chemical Abstracts Service, Columbus, Ohio, US; Palladina, L.I. et al., Effect of some products of tissue autolysis on the retrieved from STN & Ukrain. Biokhim Zhur. (1956) 28, 442-8; Russian Summary, 449-50.

Supplementary Partial European Search Report for European Application 0095323.1 dated Nov. 29, 2002.

Eguchi et al., "Elicitation of lens formation from the 'ventral iris' epithelium of the newt by a carcinogen, N-methyl-N'-nitro-N-nitrosoguanidine," *J. Embryol. Exp. Morphol.*, vol. 30, No, 1, pp. 63-71 (1973).

Frost et al., "Effects of Exogenous Guanosine on Chromatophore Differentiation in the Axolotl," *Pigm. Cell Res.*, vol. 1, pp. 37-43 (1987).

Levine et al., "Topical Vitamin-A Acid Therapy for Cutaneous Metastatic Meianoma,"*The Lancet*, pp. 224-226 (1980).

Pope et al. "7-Allyl-8-oxoguanosine (loxoribine) inhibits the metastasis of B16 melanoma cells and has adjuvant activity in mice immunized with a B16 tumor vaccine," *Cancer Immunology and Immunotherapy*, vol. 38, pp. 83-91 (1994).

Sidi et al., "Guanosine Potentiates the Antiproliferative Effect of Cytosine-(3-D-Arabiofuranosidine Melanoma Cell Lines,"*Cancer Investigation*, vol. 11, No. 5, pp. 523-529 (1993).

Sondek et al., "A phase II evaluation of ali-*trans*-retionic acid plus interferon alfa-1 in stage IV melanoma: A southwest oncology group study," *Cancer Journal from Scientific American*, vol. 5, pp. 41-47 (1999).

Spanjaard et al., "Clone 10d/BM28 (*CDCL1*), an Early S-Phase Protein; Is an Important Growth Regulator of Melanoma," *Cancer Research*, vol. 57, pp. 5122-5128 (1997).

Thibaudeau et al., "Cellular Plasticity Among Axolotl Neural Crest-Derived Pigment Cell Lineages," *Pigm. Cell Res.*, vol. 11, pp. 38-44 (1998).

U.S. Patent Office Action, for U.S. Appl. No. 13/023,152, mailed Mar. 22, 2012, of which this application is a continuation of.

United States Office Action dated Aug. 8, 2011, which issued during the prosecution of U.S. Appl. No. 13/023,152, of which the present application is a continuation.

United States Office Action dated Oct. 14, 2010, which issued during the prosecution of U.S. Appl. No. 12/775,609, to which the present application claims priority.

United States Office Action dated Nov. 9, 2009, which issued during the prosecution of U.S. Appl. No. 11/557,772, to which the present application claims priority.

United States Office Action dated May 22, 2009, which issued during the prosecution of U.S. Appl. No. 11/557,772, to which the present application claims priority.

United States Office Action dated Sep. 4, 2008, which issued during the prosecution of U.S. Appl. No. 11/557,772, to which the present application claims priority.

* cited by examiner

FIG. 1
FIG. 2
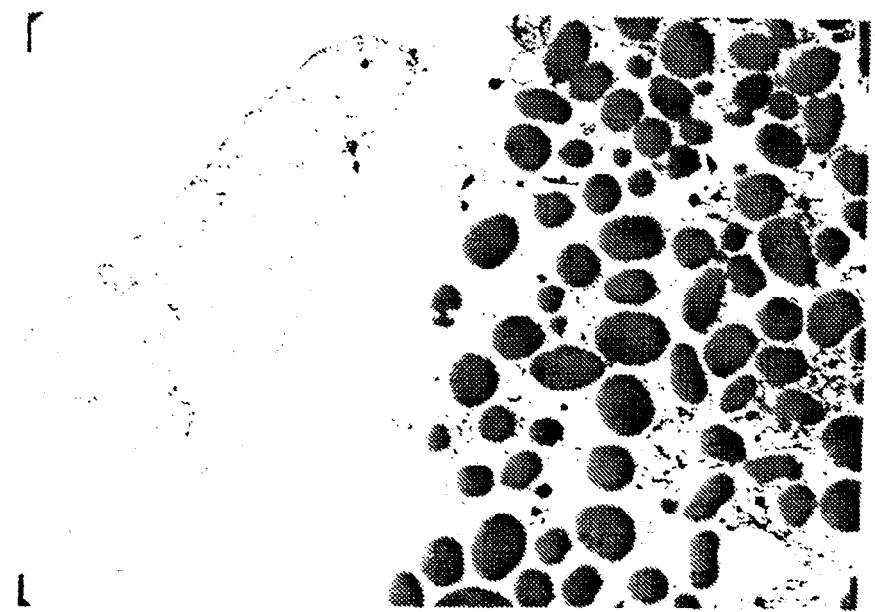

METHODS FOR TRANSDIFFERENTIATION OF BODY TISSUES

CROSS-REFERENCE TO RELATED APPLICATIONS

This application is a continuation of U.S. Utility patent application Ser. No. 13/023,152, filed on Feb. 8, 2011, which is a continuation of U.S. Utility patent application Ser. No. 12/775,609, filed on May 7, 2010, which is a continuation of U.S. Utility patent application Ser. No. 11/557,772, filed on Nov. 8, 2006; which is a continuation of U.S. Utility patent application Ser. No. 10/600,745 tiled on Jun. 19 2003 (now U.S. Pat. No. 7,176,189, issued Feb. 13, 2007); which is a divisional of U.S. Utility patent application Ser. No. 09/856,881, filed May 24, 2001 (now U.S. Pat. No. 6,670,397, issued Dec. 30, 2003); which is a National Stage application of PCT/US00/21015, tiled Jul. 31, 2000; which application claims priority to U.S. Provisional Patent Application Ser. No. 60/146,272, tiled on Jul. 29, 1999 and U.S. Provisional Patent Application Ser. No. 60/168,558, filed on Dec. 2, 1999. Each of the above-identified patent applications is incorporated herein, by reference, in their entirety.

BACKGROUND OF THE INVENTION

Multiple invertebrates and several vertebrate species are known to possess the ability to regenerate lost body parts (Goss, *Clin. Orthop.,* 1980, 151:270-282; Kawamura and Fujiwara, *Sem. Cell Biol.,* 1995, 6; 117-126; Tsonis, *Devel. Biol.,* 2000, 221:273-284). Thus, invertebrates can reconstruct the whole body from small pieces (Kawamura and Fujiwara, supra). Examples of regeneration in vertebrates include (i) rabbits and bats which can fill in holes punched through their ears; (ii) adult salamanders which can regenerate a complete limb after amputation; and (iii) mice which can replace the tip of a foretoe when it is amputated distal to the last joint (Goss and Grimes, *Am. Zool.,* 1972, 12:151; Neufeld and Zhao, pp. 243-252, In: *Limb Development and Regeneration,* Fallon ed., John Wiley and Sons, 1993).

In humans, the fingertips of young children have also been shown to regrow after amputation distal to the last joint (Goss, supra; Illingworth, *J. Ped. Surg.,* 1974, 9:853-858). Two factors have been shown to be important for this regeneration: (1) the opened surface of a fresh wound that can be covered by epidermal epithelium originating from the margins of the amputation site (Stocum, pp. 32-53, In: *Regulation of Vertebrate Limb Regeneration,* Sicard ed., Oxford Univ. Press, 1985), and (2) an adequate nerve supply at the wound surface (Singer et al., *Anat. Embryol.,* 1987, 177:29-36).

The cellular mechanisms underlying regeneration have been studied for a number of years, and there appear to be some conserved features between species. In vertebrates, there two ways in which regeneration occurs. In some tissues, multipotent quiescent stem cells become activated by damage and proliferate to produce new cells of several different terminally differentiated phenotypes. Alternatively, there may be a change in the phenotype of the functional, fully differentiated cells, such that they lose many of their differentiated characteristics, and proliferate to form new fully differentiated cells of other phenotype. This latter process has been termed Atransdifferentiation@ (Okada, pp. 349-380, In: *Current Topics in Developmental Biology,* Denis-Donini et al. eds., Acad. Press, 1980; Okada. *Trans-differentiarion,* Oxford Sci. Publ., 1991).

Retinal regeneration represents an example of the regenerative process that can occur either through stem cells or via transdifferentiation; depending on the species. Thus, teleost fish contain a population of retinal progenitor stem cells that can act as a source of new retinal neurons following damage (Hitchcock and Raymond, *Trends Neurosci.,* 1992, 15:103-108). In contrast, amphibians and embryonic chicks can regenerate their retina by a process that involves transdifferentiation of the cells in the pigment epithelium (RPE) to neural retinal progenitors (Reh and Pittack, *Sem. Cell Biol.,* 1995.6:137-142).

The existence of regeneration by transdifferentiation was questioned for a long time as it was not consistent with the classic view of differentiation, according to which a once acquired cellular phenotype was considered to be fixed due to irreversible changes in the gene expression pattern. However, the development of in vitro cell culture systems allowed the unequivocal experimental demonstration of regeneration by transdifferentiation. Thus, it has been shown that cultured fully differentiated pigmented epithelial cells of adult newt iris have the ability to dedifferentiate and proliferate to form a new tissue, lens (Eguchi el al., *Proc. Natl. Aced. Sci. LISA,* 1974, 70:5052-5056; Abe and Eguchi, *Dev. Growth Diff.,* 1977, 19:309-317).

Both in vivo and in vitro studies have demonstrated that cytoplasmic signals and changes in the gene expression (e.g., selective gene activation and/or silencing) caused by interactions with growth factors and components of the extracellular matrix are important in the control of cellular transdifferentiation (Kodama and Eguchi. *Sem. Cell Biol.,* 1995, 6:143-149; Rao and Reddy, *ibid.,* 151-156). Thus, it has been Shown that copper deficiency in rats leads to loss of cell-cell interactions altered microenvironment and global apoptosis of acinar cells in the pancreas which, in tarn, causes oval and ductal pancreatic cell: to undergo active proliferation resulting in their transdifferentiation into liver hepatocytes (Rao and Reddy, supra). In another series of experiments conducted with the neural crest-derived pigmented skin cells (chromatophores) of the Axolotl (*Ambystoma mexicanum*), it has been shown that the addition of guanosine can cause these cells to transdifferentiate from one pigmented cell type to another (Frost et al., *Pigm. Cell Res.,* 1987, 1:37-43; Thibaudeau and Holder, *Pigm. Cell Res.,* 1998, 11:38-44).

It is believed that the replacement of complex appendages (i.e., epimorphic regeneration) following amputation in lower vertebrates also occurs by transdifferentiation (Goss, supra). Thus, during epirnorphic regeneration, epidermal wound healing is followed by the accumulation of dedifferentiated blastemal cells beneath the wound epidermis. These blastemal cells are thought to originate by the dedifferentiation of the mesenchymal and Schwann cells of the stump tissue (Brockes, *Science,* 1984, 225:1280-1287) which then dedifferentiate to reconstruct the limb tissue (Singer et al., *Anat. Embyol.,* 1987, 177:29-36).

BRIEF SUMMARY OF THE INVENTION

The present invention is directed to methods for inducing mammalian cells to transdifferentiate and to uses of such cells. Cells which display morphological and functional characteristics representative of terminal differentiation are induced to change into other cell types. These cells may be derived from a plurality of organisms and from any body tissue.

In one aspect, the present invention provides a method for transdifferentiating mammalian cells comprising the steps of:
(a) contacting said cells with an effective amount for dedifferentiation of an agent which causes dedifferentiation of said cells, producing dedifferentiated cells;

(b) contacting said dedifferentiated cells of step (a) with an amount effective for transdifferentiation of an agent which causes transdifferentiation of said dedifferentiated cells;

(c) contacting said cells from step (h) with an amount effective for stabilization of an agent which causes stabilization of cells produced in step (b); and (d) recovering stabilized, transdifferentiated cells.

In another aspect, the present invention provides a method for regenerating or creating a developmental field in a remnant of a structure in a mammal, said structure having been partially destroyed, comprising the steps of:

(a) dedifferentiating said remnant of said structure;

(b) transdifferentiating said remnant of said structure of step (a); and (c) stabilizing said remnant of said structure of step (b); thereby creating a developmental field in said remnant.

In yet another aspect, the present invention provides a method for treating cancer in a mammal comprising contacting said cancer with an amount or an agent effective to cause transdifferentiation of said cancer into benign cells.

In a further aspect, the present invention, the present invention provides a method for inhibiting the progression of an antibody-mediated autoimmune disease in a patient comprising the steps of:

(a) obtaining cells from said patient of the type which are under autoimmune attack;

(b) contacting said cells with an amount of a transdifferentiation agent effective to convert said cells to a normal phenotype;

(c) culturing said converted cells in vitro to amplify said cells;

(d) immobilizing said cells on a membrane which allows blood to enter but retains the cell; and (d) contacting said immobilized cells with said patients' blood, thereby removing said antibodies from said patients' blood.

In a still further aspect, the present invention provides a method for regenerating a tissue or organ in the body of a mammal, wherein said tissue or organ is damaged due to injury or is missing, comprising the steps of:

(a) dedifferentiating the cells at the site of injury by administering a dedifferentiating effective amount of a dedifferentiating agent;

(b) transdifferentiating said dedifferentiated cells of step (a) by contacting said cells with a transdifferentiating-effective amount of a transdifferentiation agent; and (c) stabilizing the transdifferentiated cells of step (b) by contacting said cells with stabilization-effective amount of stabilizing agent.

In a still further aspect, the present invention provides a method for producing stem cells comprising the steps of:

(a) obtaining melanocytes from a patient's skin cells;

(b) contacting said melanocytes with an agent which causes transdifferentiation; and (c) recovering stem cells.

In a still further aspect, the present invention proves a method for producing stem cells comprising the steps of;

(a) obtaining melanocytes from a patient's skin cells;

(b) contacting said melanocytes with an agent which causes transdifferentiation for a time and at a concentration effective to produce stem cells; and (c) recovering stem cells.

These and other aspects of the present invention will be apparent to those of ordinary skill in the art in light of the present description and claims.

BRIEF DESCRIPTION OF THE DRAWINGS

FIG. 1 is an election micrograph taken from an Axolotl which was fed GMP (described in Example 5B). On the left is a process of a xanthophore. On the right is a process of a melanophore. pt=pterinosome; m=melanosome; p=premelanosome; * marks artifacts due to tears in the plastic. The melanosomes are oval or round structures build on an internal lattice, and partially composed of numerous small round bodies as seen in the marked premelanosome. The pterinosomes appear as vacuoles with wispy or concentric fibrillar material.

FIG. 2 is the same animal as in FIG. 1. Pterinosomes and melanosomes are seen in the same cell. Furthermore, a hybrid organelle is seen at the bottom of the picture. This cell is judged to be transdifferentiating based on the following criteria: (a) presence of numerous pterinosomes and melanosomes in the same cell, and (b) presence of some organelles with characteristics suggestive of both melanosomes and pterinosomes.

DETAILED DESCRIPTION OF THE INVENTION

Figure 3:
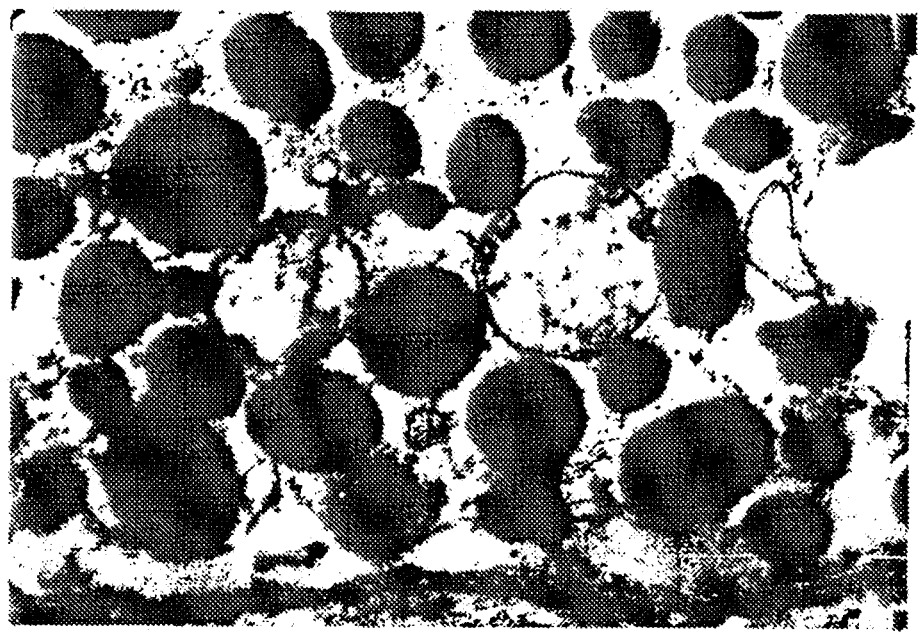
FIG. 3 is a blow-up of the hybrid organelle seen at the bottom of FIG. 2.

All patent applications, patents, and literature references cited herein are hereby incorporated by reference in their entirety. In case of conflict, the present description, including definitions, will control.

Definitions

As used herein, the following terms are defined for purposes of this invention.

ATransdifferentiation@ refers to the capacity of differentiated cells of one type to lose identifying characteristics and to change their phenotype to that of other fully differentiated cells, ACell destabilization@ or Adedifferentiation@ refers to the loss of phenotypic characteristics of a differentiated cell by activating or deactivating genes or metabolic pathways.

ACell stabilization@ refers to the maintenance of phenotypic characteristics of a differentiated cell by maintaining, activating or deactivating genes or metabolic pathways.

AMorphogenetic field@ refers to a group of cells which have the capacity to give rise to a particular organ (e.g., pancreas, liver) or appendage (e.g., limb, tail) during embryogenesis or subsequent regeneration. It can be alternatively called a Adevelopmental field,@ or Aepimorphic field.@ or Aprimary field@ (Hopper and Hart, *Foundations of Animal Development*, Oxford Univ. Press. 1980, p. 314).

AToxin@ refers to a substance which is poisonous to a cell. A toxin may or may not be a protein. Non-limiting examples of toxins include: (a) heavy metals such as cadmium, copper and zinc; (b) strong acids or bases such as hydrochloric acid (<pH 5) or sodium hydroxide (>pH 8); (c) ATP inhibitors, such as ATPase, and (d) poisons that destabilize membranes, such as detergents, The Aneural crest@ refers to ectoderm-derived cells which during development of the embryo are found interposed between the neural tube and the ectoderm (LeDouarin, *The Neural Crest*, Cambridge Univ. Press, 1982). Cells of the embryonic neural crest give rise to a wide range of tissues which include: (a) cells of the peripheral nervous system; (b) dermal hone; (c) cephalic connective tissue; (d) pigment cells; (e) calcitonin secreting cells; (f) meninges; (g) Schwann cells: (h) odontoblasts, and (i) adrenal medulla.

AChromatophores@ refers to specialized cells for animal coloration which are usually of neural crest origin. Each of the chromatophores has a pigment containing organelle derived from the endoplasmic reticulum. There are three classes of chromatophores that are defined based on the type of pigment contained within these organelles: melanophores, xanthophores, and iridiophores (Ide, *Curr. Topics Dev. Biol.*, 1986, 20:79-87; Bagnara, The Neural Crest as a Source of Stem Cells, pp. 57-87, In: *Developmental and Evolutionary Aspects of the Neural Crest*, laderson ed., John Wiley and Sons, 1987).

AMelanophores@ are chromatophores which contain the pigment melanin. The melanin is contained in organelles called melanosomes.

AXanthophores@ are yellow, orange or red colored chromatophores. The pigments of xanthophores are a class of cyclic compounds called pteridines. Pteridines, which are derived from guanosine triphosphate, are contained in an organelle called a pterinosome. Xanthophores also sometimes contain an organelle called a carotenoid droplet.

Atridophores@ contain a pigment composed of crystalline deposits of purines. The crystalline deposits are contained in organelles called reflecting platelets, so named because the organelles scatter and reflect light.

ARemnant@ is a portion of a structure which remains after damage by amputation, disease or other agents.

APartially destroyed@ refers to a structure (e.g. tissue organ or appendage, such as a limb) in which (a) a percentage of the structure=s mass is removed, or b) the internal pattern and numbers of cells comprising the structure are damaged or killed while some vestigal cells and/or pattern remains.

DETAILED DESCRIPTION OF PREFERRED EMBODIMENTS

It is envisioned that the present invention will be used to produce cells by transdifferentiation for the replacement of body tissues, organs, components or structures which are missing or damaged due to trauma, age, metabolic or toxic injury, disease, idiopathic loss, or any other cause.

In another aspect, transdifferentiation is used to regenerate external structures such as fingers, toes or parts of such structures.

In still another aspect, transdifferentiation is used to treat cancer by making cancer cells adopt non-malignant phenotypes.

Finally, according to the present invention transdifferentiation is used to provide autologous cells for removal of harmful auto-antibodies.

Without wishing to be bound by theory, it is believed that the methods detailed for (1) regeneration of body parts and (2) transdifferentiation of tissues/cells represent two complementary, intertwined, and indispensable aspects of a biological entity which is termed a Amorphogenetic field.@ The methods herein described cause reconstitution and, in some cases, creation, of morphogenetic fields.

Morphogenetic fields, by their nature, are capable not only of (1) regeneration of lost body parts and (2) transdifferentiation of histological, cytochemical, ultrastructural, and molecular phenotypes, but also of (3) intrinsically recognizing and restoring parts in their proper position, That is to say, morphogenetic fields preserve the original anterior/posterior, dorsal/ventral, and right/left axes for a regenerating limb. This property, which is variously referred to as Apositional information® or sometimes Ahandedness@ is a function of the expression of the appropriate genetic program governing a particular morphogenetic field. (French et al. *Science*, 1976, 1.93:969-981; Wolpert, *J. Theor. Biol.*, 1969, 23:1-47). The methods herein described for (1) and (2) above, representing progression of the program for selective gene activation appropriate for a particular morphogenetic field (e.g., right forelimb) therefore inherently also accomplish (3) restoration of the structure with accurate positional information of its components. For example, if a limb is amputated at the distal humorous on a right forelimb, the regenerating radius and ulna will be in the appropriate locations for a right forelimb and not a left forelimb.

Therefore, the methods described herein provide reconstitution (e.g. limb regeneration) and, in some circumstances, creation (e.g., liver from pancreas remnant) of morphogenetic fields.

According to the present invention, regeneration via transdifferentiation may be performed in situ (e.g., at the site of trauma or injury).

Alternatively, an organ or tissue can be transdifferentiated/regenerated in vitro, and then introduced back into the body. Thus, in one of the preferred embodiments human pancreatic cells are regenerated and transdifferentiated into hepatocytes by treatment with various agents in cell culture, plated in a self-degrading plastic container containing a seven day supply of culture medium, and then sewn adjacent to a liver blood vessel which vascularizes the new tissue, incorporating it in the liver.

The use of in vitro transdifferentiation for regeneration of tissues and organs insures the autologous nature of the transplant and provides a great advantage, when employed in medical practice, by avoiding the need for immunosuppression and decreasing the chances of transplant rejection.

In a preferred embodiment of the present invention, the method of transdifferentiation comprises the steps of (a) destabilizing or dedifferentiating the cells, (b) transdifferentiating the destabilized cells, and (c) stabilizing the transdifferentiated cells, causing them to differentiate.

In practicing the present invention, the tissue to be transdifferentiated/regenerated can be derived from ectoderm, mesoderm, endoderm, neural crest or extra embryonic membranes.

Destabilization/dedifferentiation may be accomplished, by, but is not limited to the following:

1. Administering an agent to cells of the site of injury or in culture. Agents to induce destabilization, include but are not limited to, retinoids (e.g. retinoic acid), 12-O-tetradecanoylphobol-13 acetate (TPA), 0.1 M hydrochloric acid (pH<5), hypertonic saline (saturated NaCl), copper chelators (such as triethylenetetramine tetrahydrochloride), and heavy metals, such as copper, zinc, or cadmium. The amount of toxin administered varies from toxin to toxin but will generally be 1-100 µg/ml in cell culture.

2. Disintegration of the extracellular matrix (e.g. by administering hyaluronidase or collagenase).

3. Physical separation of cells by mechanical or enzymatic methods (such as trypsinization, EDTA treatment, or repeated needle trauma).

4. Trauma (see below).

The preferred method of destabilization depends on the accessability of the target tissue, the nature of the extracellular matrix structure and components which hold it together. For example, when performing destabilization of skin cells, trypsinization of the basement membrane is often the method of choice.

Trauma of any kind, including, injury caused by surgery, laser, penetration (e.g. needle), chemical, heat, visible or nonvisible (e.g. UVA) light, x-radiation, infection, toxin, or immune response, tends to be very effective in causing destabilization in many tissues. In fact, trauma is the most common natural destabilizing agent in animals that are able to naturally regenerate organs and body parts (e.g., a predator amputating a lizard tail or amphibian limb). Therefore, trauma can be used as a starting step in the regeneration process. Some of the modes by which trauma stimulates destabilization includes the following:

(1) Trauma of the epithelium will usually disrupt the basement membrane leading to changes in the basement membrane components such as fibronectin and laminin. These changes, in turn are known to affect synthesis of proteins, mRNA, and DNA (*Cell Biology of Extracellular Matrix*, Hay ed., Plenum Press, 1981).

(2) Trauma may lead to changes in cells=microenvironment by affecting neighboring cells which secrete growth factors, cytokines, immunoglobulins, or other substances that affect the differentiated state of the cell under consideration and may cause it to dedifferentiate and perhaps proliferate in the absence of normal levels of these factors. In addition, trauma may cause cells to come into contact with cell types or body fluids which they normally do not come into contact with, and this may also cause destabilization. All these effects on cells=microenvironment result in changes in intracellular signaling pathways leading to changes in protein synthesis and gene expression.

(3) Trauma, by changing the cell microenvironment, leads to changes in cell shape (e.g., flattened vs. rounded) causing changes in protein and nucleic acid synthesis, (Cell Biology of Extracellular Matrix, supra) and thus affecting the cells=differentiated state. Changes in cell shape can be dependent on such factors as the adhesive characteristics of the surface (e.g. cell membrane, extracellular matrix, other surrounding cells).

(4) Trauma may cause the release of substances called "wound hormones" which may cause destabilization.

Some examples of how trauma may be used to stimulate destabilization in a mammal are provided in Example 18, below.

According to the present invention, following destabilization, the cells are contacted with an effective amount of a transdifferentiation agent. Non-limiting examples of transdifferentiation agents include: guanosine, phenylthiourea or TPA.

Finally, the cells are contacted with an effective amount of a stabilizing and differentiating agent. Non-limiting examples include: beta-carotene, retinoids, riboflavin, and pteridines.

All of the above-mentioned destabilizing, transdifferentiating and stabilizing reagents can be obtained commercially (e.g., from Sigma Chemical, St. Louis, Mo.).

According to the present invention, effective amounts of these reagents would broadly range between about 1 and about 100 µg/ml in the cellular microenvironments (e.g., cell culture medium) or between about 0.5 and about 1,000 mg/kg body weight in a recipient animal.

It should be noted that all reagents for transdifferentiation of cells in vitro are added directly to their culture medium. In mammals undergoing regeneration in situ, the preferred route of administration of the destabilization and transdifferentiation agents is topical. When the organ or tissue treated is internal, direct administration is accomplished by needle or catheter, or systemically.

The stabilizing/differentiation agents are preferably administered systemically, most preferably orally, enterally, by inhalation, by aerosol, rectally, etc.

In an alternative embodiment of the invention, a transdifferentiation agent and stabilizing/differentiating agent are administered substantially simultaneously instead of sequentially, e.g., guanosine is administered together with beta-carotene. Preferably the two agents are administered for a period of hours or days.

In another alternative embodiment of the invention, the same compound is used for the transdifferentiating step and stabilizing steps (e.g. relatively large amounts of retinoic acid [$10^{-4}$M in cell culture]). In this embodiment, the dedifferentiating step (e.g., amputation by mechanical trauma, blade or needle sticks) precedes the addition of the transdifferentiation/stabilization agent.

Each of the steps in the process of transdifferentiation/regeneration takes from how's to days to completion depending on the agent used, its dose, method of administration and the target tissue. For example, to stimulate limb regeneration in a mammal, the hypertonic saline regimen developed by Rose for newts (*J. Exp. Zool.*, 1944, 95:149-170) or repeated sticks with a 25 gauge needle are used thrice daily for three days after amputation.

According to the present invention, the cell destabilization phase (which can be monitored histologically [e.g., using light microscopy] and/or biochemically) is considered completed when cells have lost the morphological and biochemical characteristics which define their phenotype. These cells start to resemble blastema cells (i.e., they have a high nucleus to cytoplasm ratio and/or lack morphological characteristics of differentiated cells). For example, in the stump of an amputated limb, such cells are seen about two weeks after amputation in the newt *Triturus viridescens*.

The transdifferentiation phase is considered completed when cells acquire some of the morphological and biochemical characteristics which define their new phenotype. For example, when characteristic striated phenotypes are seen in putative muscle cells, or axons and dendrites are seen in putative neurons.

The stabilization/differentiation phase is considered completed when cells have acquired all of their terminally differentiated morphological and biochemical characteristics (e.g., when one can microscopically and/or biochemically detect the internal storage organelles containing the stabilization/differentiation agents, such as carotenoid droplets, deposits of riboflavin, or pteridines in pterinosomes).

In a still further embodiment, the present invention provides a method for identifying novel compounds that possess transdifferentiation and/or stabilization capacity. Non-limiting preferred screening systems for said candidate compounds are: (a) optic cup-derived retinal pigmented epithelium (RPE) cells of the newt or mammalian eye transdifferentiating into lens; (b) RPE of the newt or mammalian eye transdifferentiating into retinal neurons: (c) mammalian pancreatic cells transdifferentiating into hepatocytes; (d) neural crest-derived Axolotl chromatophores transdifferentiating into another pigmented cell type, and (e) mammalian terminally differentiated neural crest-derived cells transdifferentiating into other types of neural crest derivatives (e.g., melanocytes to neurons, cephalic connective tissue to bone, Schwann cells to neurons or bone, etc.). A preferred screening system, using Axolotl is presented below in Example 5.

Based on the ability of some previously identified compounds to act as universal transdifferentiation agents in various systems (e.g., guanosine in Axolotl chromatophore system, in newt, and in mammalian RPE systems; copper depletion in mammalian pancreas-to-hepatocyte and mammalian RPE systems), any agent which causes transdifferentiation and/or regeneration in any of the experimental systems, will be a candidate for causing transdifferentiation and regeneration in other tissues and in other animals. In addition, agents that cause cells (e.g., neural crest cells) to differentiate along a particular pathway during embryogenesis will be candidates for transdifferentiation agents in adults.

Thus, in one embodiment Stage I candidate compounds will be tested for their ability to convert mature adult human skin melanocytes into neural stem cells. A dose response curve will be generated by concurrently incubating, in separate vials, cultured cells with a test substance at concentrations ranging between about $10^{-3}$ μg/ml and about 100 μg/ml, the concentration increasing by half log units. Cells will be incubated with the test compounds from one to 21 days, Cells will be examined for evidence of transdifferentiation by light or electron microscopy, biochemical tests, and immunological labeling with the criteria of transdifferentiation depending on the stem cells used and the new tissue type desired. For example, the transdifferentiation of melanocytes to neural crest stem cells, will be observed as a loss of melanosomes and melanin.

In a still further embodiment, Stage II candidate compounds will be tested for their ability to convert the cells resulting from Stage I into terminally differentiated phenotypes, such as neurons, Schwann cells, cartilage cells, and fibroblasts. A dose response curve will be generated by concurrently incubating, in separate vials, cultured cells which have been previously transdifferentiated, with a second test substance at concentrations ranging between about $10^{-3}$ μg/ml and about 100 μg/ml, the concentration increasing by half log units. Cells will be incubated with the test compounds from one to 21 days. Cells will be examined for evidence of dedifferentiation by light or election microscopy, biochemical tests, and immunological labeling with the criteria of transdifferentiation depending on the stem cells used and the new tissue type desired.

Examples of chemicals which can be screened by the above methods include: purines and pyrimidines, nucleosides and their derivatives, retinoids, carotenoids, laminin, fibronectin, growth factors, cytokines, ommochromes, thioureas, chelating agents, and metals (such as zinc, copper, cadmium). Depletion or supplementation of substances normally present in culture media can also be screened by the above method (Brent et al., *Am. J. Pathol.*, 1999, 137:1121-1142).

Based on the above-mentioned experimental evidence from various transdifferentiation systems, low toxicity and good solubility properties, guanosine is a particularly preferred compound for use as a transdifferentiation agent in the present invention. Thus, as shown below in Example 1, in gerbils oral administration of guanosine (a transdifferentiation agent) followed by beta-carotene (a stabilizing agent) after surgical removal of a lens, led to regeneration of the lens from RPE. It should be noted that in this case, the destabilization/dedifferentiation agent was the trauma caused by the surgery used to remove the lens.

In further alternative embodiments guanosine may be substituted for with guanosine monophosphate (GMP), guanosine diphosphate (GDP), guanosine triphosphate (GTP), adenosine, cytosine, thymidine, uridine and their phosphates, or catecholamines (such as norepinephrine and epinephrine).

In light of the above-mentioned experimental evidence, copper is another preferred compound for use as a transdifferentiation agent in the present invention, Agents which affect copper levels in the body (and in specific tissues) thus may also have activity as transdifferentiation agents. Some of the substances that cause changes in copper levels include the following:

(I) Metals such as zinc, cadmium and iron (Linder and Hazegh-Azam, *Am J. Clin Nutr,* 1996, 63:797 S-811S);

(II) Copper chelators such as trien (Rao and Reddy, supra), penicillamine (Brewer, *Copper Transport and Its Disorders,* Leone and Mercer eds., Plenum Publishers, 1999);

(III) Agents that affect the absorption of copper such as zinc acetate (Brewer, supra);

(IV) Enzymes that affect the metabolism of copper and/or use copper as their cofactor (e.g., tyrosinase, superoxide dismutase, hyaluronidase); copper binding proteins (e.g., ceruloplasmin or metallothien) (Linder and Hazegh-Azam, supra);

(V) Substances that affect the synthesis or degradation of copper binding proteins/enzymes (e.g., retinoic acid [Song and Levenson, *Int. J. Vitam. Nate. Res.* 1997, 67: 141-144]);

(VI) Copper binding non-proteinaceous compounds (e.g., ascorbate [Itoh and Eguchi, *Dev. Biol.,* 1986, 1.15:353-362; Droudin et al., *Free Radic Biol Med.* 1996, 21:261-273], various thioureas [Masuda and Eguchi, *Cell Structure and Function,* 1984, 9:25-35], guanosine adenosine [Masuda and Eguchi, *Inorganic Chemistry,* 1990, 29:3631], cytosine [Palaniandavar et al. *J. Chemical Soc.,* 1996, 7:1333] and their phosphates).

Copper deficient diets (Yoshida et al., *J. Neurooncol.,* 1993,17:91-97) and copper depleted media (Percival and Layden-Patrice, *J. Nutr.,* 1992, 122:2424-2429) for cells are other methods for changing copper levels.

One way by which the dedifferentiating and transdifferentiating effect of copper is believed to be exerted is by its acting as a cofactor of enzymes which generate products characteristic of the terminally differentiated cells (e.g., tyrosinase that leads to production of melanin). Copper is also thought to cause transdifferentiation by affecting the amount of free guanosine (Tu and Friederich, *Biochem.,* 1968, 7:4367-4372; Maskos. *Acta Biochemica Polonica,* 1978, 2:101-111) and by direct binding to DNA and RNA (lyengar, *Acta Anat.,* 1983, 115:357-360; Wong et al., *Can J. Biochem.,* 1.974, 52:950-958; Sorokin et al., *J. Inorg. Biochem.,* 1.996, 63:79-98) which leads to their break-down (i.e., stand scission and fragmentation; Yamafuji et al., *Enzymologia,* 1971, 40:107-119; Dowjat et al., *BioMetals,* 1996, 9:327-335). Finally, copper is angiogenic (Brem et al., *Am. J. Pathol.,* 1990, 137:1121-1142; Yoshida et al., *Neurosurgery,* 1995, 37:287-293) and thus supplementation of copper encourages growth of tissues and differentiation. It can be therefore concluded that other substances which act in a manner similar to copper would be candidate transdifferentiation agents.

Another group of preferred compounds for use as transdifferentiation agents according to the present invention includes substances involved in biochemical pathways producing pigments (such as melanin, ommochromes, hemocyanin, carotenoids, flavonoids, and pteridines). According to the present invention, the preferred experimental system to test these compounds is either Axolotl chromatophore system, or Kupffer stem cell system in which stem cells differentiate into the full line of neural crest derivatives (Nozue, *Acta Anat.,* 1990, 107:188-197; Labat et al. *Biomed Pharmacother.,* 2000, 54:146-162).

Novel dedifferentiating, transdifferentiating and stabilizing compounds identified according to the method disclosed herein may be further tested for their effectiveness and pharmaceutical acceptability. Preferred agents will meet the following criteria:

1. The ability to produce or regenerate tissues/organs from a repeated toxic or traumatic injury which function most like the original (e.g., regeneration of a lens in a gerbil which is most like the original in transparency, geometric shape, ability to focus light, accommodate, etc.):

2. Minimal local and systemic toxicity (e.g., guanosine and beta-carotene);

3. The ability to act rapidly and in relatively small amounts;

4. The ability to be made into easily administered pharmaceutical preparations.

Without wishing to be bound by theory, it is believed that the regenerative ability of animals is critically dependent on their diet. Organisms which ingest food that includes large quantities of purines, pteridines and carotenoids, or precursors of each of these compounds, maintain multi-potent cells which may more easily undergo transdifferentiation. The effect of diet on transdifferentiation is exemplified by the loss of regenerative ability as amphibians mature from larvae (herbivorous diet) to adult (carnivorous diet), and by greatly decreased ability of vertebrates which have a diet deficient in carotenoid containing foods, to regenerate lost body parts.

Thus, according to the present invention, the optimal conditions for regeneration in vertebrates, and specifically in mammals include:

6. A diet supplemented for a month prior to injury with beta-carotene (1000 mg/kg), which includes the 9 cis isomer as well as other carotenoids such as lutein, and zeaxanthin; under these conditions optimal regeneration will be observed in mammals that are high carotene accumulators (such as gerbils and humans); human patients who consume large amounts of carotenoid-containing vegetables are particularly good candidates for the methods disclosed herein;

7. Preparing the site of regeneration by local topical application to the wound surface of a saturated HCl solution to facilitate electrical properties (e.g., by immersion of the digit stump into hypertonic saline for 1 hour, twice per day):

8. A photo period of 8-16 hours light per 24 hours depending on the tissue and species, with a source of natural light which includes the UV spectrum during the dedifferentiation step.

When employing conditions listed above, the optimal regeneration will be observed in small structures which have a high density of chromatophores, such as infant=s fingers or toes accidentally amputated at any level including the metacarpal-phalangeal joint.

In order to produce a particular cell type, it is necessary to select a particular agent, close and exposure time for each of the agents during the following phases: destabilization, dedifferentiation, transdifferentiation, stabilization.

To select the appropriate treatment, a matrix of effects is created by systematically varying each factor above. For example, if it is desired to produce a particular type of spinal motor neuron using retinoic acid as the agent for transdifferentiation. A matrix will be set up wherein retinoic acid is tested at different half log incremental concentrations, e.g., ranging from $10^{-9}$ molar to $10^{-4}$ molar, with other factors being held constant. For each of these culture tubes, the cells resulting from the stabilization phase will be tested histochemically for the characteristics of the spinal motor around. Once a particular concentration of retinoic acid is selected in this manner, the process will be fine-tuned by setting up a matrix of exposure times which are systematically incremented e.g. exposure times of doses from one day to seven days in one day increments. Agents during the destabilization and stabilization phases will similarly be varied to choose the exactly correct agent, its dose and exposure times to result in a particular cell type.

The starting point to use for the range of dose can be determined as follows: if the agent has ever been reported used in cell culture of some type, the starting dose will be about the dose reported in the literature. If the agent has not been used in the cell culture this starting dose will be that of any similar chemicals reported in the literature used in cell culture. If the agent has never been reported, a systematically incremented range, either in molar concentrations or by weight is chosen. If the cells at a particular dose die, then the dose is too high.

If the cells at a particular dose show no effect, then the dose is too low, and by bracketing results in this matter and iterating the procedure, the proper dose will be selected.

In those cases where the agent is not a chemical, that agent will still be systematically varied during the testing process. For example, if the agent is trauma created by the use of a scalpel, the size of the incision will be systematically varied in a matrix, other factors held constant, and the resulting cell types identified and classified histochemically or immunocytochemically.

In another embodiment, the present invention provides a method for screening anti-cancer agents by testing their ability to induce transdifferentiation of cancer cells (e.g., melanoma cells) into benign, terminally differentiated cells. In a preferred embodiment, the least toxic and the most efficient transdifferentiating agent is first selected using in vitro cultured cancer cells derived from a particular patient. The selected agent is then administered to patient, and the regression of cancer is monitored by standard techniques. In this way an optimum individualized anti-cancer treatment is achieved.

In a still further embodiment, the present invention provides a method for inhibiting the progression of an antibody-dependent autoimmune disease (such as lupus or myasthenia gravis). Said method involves lowering the titer of autoreactive antibodies present in the blood of a patient suffering from an autoimmune disease by regular dialysis of the blood through the matrix containing immobilized patient=s cells reactive with these antibodies. According to the present invention, the unlimited supply of such immobilized cells could be obtained by in vitro transdifferentiation of cultured cells derived from the same patient. Because these are the patient=s own cells, no new unwanted antibodies would be generated, and the adverse effects would be minimized.

The present invention is described below in working examples which are intended to further illustrate the invention without limiting the scope thereof.

EXAMPLE 1

Stimulating the Regeneration of a Lens in a Gerbil

Materials and Methods

The effect of guanosine and beta-carotene on stimulating the regeneration of an amputated lens was examined in Mongolian Gerbils (*Meriones unguiculatus*).

Animals: 4 week-old Mongolian Gerbils from Charles River Laboratories Wilmington, Mass.

General Conditions:
Temperature:
Days 1-23: 22° C.
Day 24: 26° C.
Day 25: 29° C.
Day 26: 32° C.
Days 27-61: 35° C.
Photoperiod: 12 his light; 12 his dark

TABLE 1

Gerbil Protocol Groups

| Group No. | Diet Days 1-33 | Diet Days 34-62 | Males | Females |
|---|---|---|---|---|
| 101 | A* | A | 4 | 4 |
| 102 | A, CT | A | 5 | 5 |
| 103 | A, CT, G | A | 5 | 5 |
| 104 | A, CT, B | A, B | 5 | 5 |
| 105 | A, CT, G, B | A, B | 5 | 5 |
| 106 | A, G | A | 4 | 4 |
| 107 | A, G, B | A, B | 4 | 4 |
| 108 | A, B | A, B | 4 | 4 |
| Totals | | | 36 | 36 |

*A = AIN 93G (a standard rodent diet available from Dyets, Inc., Bethlehem, PA),
C = copper deficient diet with 30% of normal copper (normal copper = 6 mg/kg diet; copper deficient = 30% normal = 1.8 mg copper per kg diet),
T = 0.5% Triethylenetetramine Tetrahydrochloride (trien),
B = 1% Dunaliella Beta-carotene with two times the usual amount of vitamin K (normal Vit. K = 0.75 mg Vit. K per kg diet; double Vit. K = 1.5 mg per kg diet),
G = 1% Guanosine.

Diets (manufactured by Dyets, Inc., Bethlehem, Pa.):

Based on usual food intakes, it is estimated that animals took in the approximate amounts of chemicals as follows. For diets containing guanosine, 1000 mg/kg/day Guanosine was consumed by each animal. For diets containing beta-carotene, 1000 mg/kg/day Beta-carotene was consumed by each animal.

Animal Laboratory Location: PSL, East Brunswick. N.J.

Histological Laboratory: Colorado Histo-Prep, Inc., Fort Collins, Colo.

The experimental animals were fed diets disclosed above to enhance dedifferentiation of the iris epithelium, and to subsequently lead to transdifferentiation of the iris epithelium into lens, A control group fed a standard AIN diet was included. Throughout the experiment, the animals were examined daily by a licensed veterinarian.

The temperature was gradually raised by 3° C. per day for four days prior to surgery to reach a temperature of 35° C. which at the time was believed to help lens regeneration. One animal from each group was sacrificed on day 27 and preserved in formalin.

The following surgical protocol was followed for each remaining animal on day 28:

1. A drop of 1% tropicamide (Bausch & Lomb, Tampa, Fla.) was placed in the right eye;
2. The animal was anesthetized by IP injection of ketamine with xylazine;
3. A diamond knife (Accutome, Malvern, Pa.) was used to make a cut in The cornea of the right eye, which was expanded with a Vanas scissors (Miltex, Bethpage. NY), so that an incision at the limbus of about 180-270° was made:
9. The lens was lifted out with a Tyrell Loop (Miltex, Bethpage, N.Y.) when gentle pressure was exerted superiorly on the eyeball by a gloved finger;
10. The removed lenses were retained in formalin.

After surgery, the animal diet was changed to the standard AIN diet, except that the group which had received AGB continued to receive beta-carotene via the AB diet. Some pellets were put in the cage so that after surgery, the animal would not have to reach up to the lid of the wire cage to get the food.

The animal eyes were examined with a magnifying glass without anesthesia weekly. However, since this animal has a dark eye, little detail could be ascertained.

On day 61, the animals were anesthetized by $CO_2$ and decapitated. The heads were placed in Davidson=s Fixative for 18 hours and then switched to neutral buffered formalin. The bodies were fixed in neutral buffered formalin.

All operated eyes fixed on day 61 were photographed. All heads from the 50 animals that survived to the end of the experiment were sent to Colorado Histoprep. The operated eye was dissected and serial 5μ sagittal sections up to the approximately mid-saggital plane were cut on a rotary microtome. For all specimens, at least 50 5μ serial sections from the mid-saggital area were prepared. The slides were processed routinely for histology and stained with Hematoxylin and Eosin.

Results and Conclusion

The operated eyes were flat after surgery, it was noticed that some animals=eyes remained partially or completely closed over the next month. However, some animals=eyes gradually became less flat and some operated to protrude almost normally.

Remarkably, about 40% of the experimental eyes showed lenses which had clearly regenerated. These often showed a stalk connecting them to the iris pigment epithelium (as seen in newt lens regeneration), as well as individual lens cells which clearly contained melanosomes, identifying them as having derived from the pigmented epithelium. These lenses extended over many histological sections, showed well formed lenses containing organized lens cells in various stages of forming fibers, as is seen embryologically. They generally were without cystic or necrotic material. When the extracted formalin-fixed whole lens was examined and compared to the histology of the regenerated lens for each animal, it was clear that in practically all cases, almost the entire lens had been removed, with the possible exception of a small amount of lens epithelium, and it was not likely that the regenerated lens was due to retained material which had proliferated. The stalk to the iris pigment epithelium, as well as individual cells containing melanosomes, showing derivation from pigment epithelium, confirmed regeneration.

Some of the operated eyes showed no lens material whatsoever (see below). Others showed lens material which had clearly been retained after the surgery. (It is well known from human cataract surgery as well as experimental models that it is often impossible to remove the entire lens so that not even a few cells of the lens epithelium remain. This is problematic clinically, since retained lens epithelium is known to proliferate and complicate the lens implants=function). Retained lens material could be identified histologically because it was generally necrotic, cystic, showed mature lens fibers, had no connection to the iris pigment epithelium, only extended over a few serial sections and by other histologic criteria. Microscopic examination and photographs of the formalin fixed extracted lenses showed that although most were removed grossly intact, all had at least small epithelial defects suggesting that some epithelial tissue had been left behind.

TABLE 2

Histological Observations on Surviving Animals

| Group No. | Diet Days 1-32 | Diet Days 33-62 | No Lens | Retained Lens | Regenerated Lens | Group Total | Percent Regenerated |
|---|---|---|---|---|---|---|---|
| 101 | A | A | 2 | 4 | 0 | 6 | 0% |
| 102 | A-CT | A | 1 | 4 | 3 | 8 | 38% |
| 103 | A-CT-G | A | 1 | 4 | 0 | 5 | 0% |
| 104 | A-CT-B | A-B | 3 | 2 | 3 | 8 | 38% |
| 105 | A-CT-G-B | A-B | 1 | 2 | 4 | 7 | 65% |

TABLE 2-continued

Histological Observations on Surviving Animals

| Group No. | Diet Days 1-32 | Diet Days 33-62 | No Lens | Retained Lens | Re-generated Lens | Group Total | Percent Re-generated |
|---|---|---|---|---|---|---|---|
| 106 | A-G | A | 3 | 0 | 3 | 6 | 50% |
| 107 | A-G-B | A-B | 4 | 0 | 3 | 7 | 43% |
| 108 | A-B | A-B | 1 | 0 | 2 | 3 | 66% |

As can be seen from the above table, none of the 6 surviving control animals (Group 101) showed regenerated lenses, although 4 showed small retained epithelium which had proliferated.

18 of the total 44 surviving experimental animals (Groups 102-108) showed regenerated lenses (41%).

There were clear differences among the groups in the quality of the regenerated lenses, with generally the best (largest, most normal appearing in overall architecture and cytology) were from group 106 guanosine diet) and group 107 (initial guanosine and beta-carotene diet).

EXAMPLE 2

Enhanced Protocols for Stimulating the Regeneration of a Lens in a Gerbil

1. An Improved Protocol for Stimulating the Regeneration of a Lens in a Gerbil

The following experiment on lens regeneration in a gerbil will be conducted to improve the experimental protocol for all further studies, and to obtain additional specimens for histological and ultrastructural analysis.

Thirty six 3-week-old Mongolian Gerbils will be obtained from Charles River Laboratories (Wilmington, Mass.) and acclimated for one week at Product Safety Laboratories (East Brunswick. NJ) animal care facilities. The temperature will be kept at 22□C throughout the experiment because it is now believed that the higher temperatures (35□C) may be unnecessary. They will be kept on a 12 hour light/dark photoperiod and fed Purina Rat Chow during the one week acclimation period. Three groups of 12 animals each will be used.

| GROUPS | DIET 1 | DIET 2 |
|---|---|---|
| (1) | Zinc Acetate 0.1% | AIN |
| (2) | Guanosine 1% + Beta-carotene 1% | Beta-carotene 1% |
| (3) | Control AIN diet | AIN |

The rationale for the use of zinc acetate rather than the previous 30% copper diet with trien is as follows. Zinc acetate is available as a prescription drug (Galzin, Lemmon Co., Sellersville, Pa.). Moreover, it has little adverse effects and thus the mortality seen from the copper deficiency diet with trien should be avoided. The dose of zinc acetate will be chosen based on published studies on its use in rodents to lower systemic copper (*Approved Package for NDA 02458 Galzin Capsules*, 1997, FDA, Rockville. MD).

The animals will receive Diet 1 for 2 weeks to promote dedifferentiation of the RPE. The animals will be anesthetized using methoxyflurane, the safest and overall most preferable anesthetic in gerbils (Norris, *Lab. Anim.*, 1981, 1.5: 153-155). Lentectomy will be performed using the procedures described in Example 1. The animals will receive Diet 2 for 6 weeks. This is 2 weeks longer than the previous protocol and should permit completion of the lens regeneration process documented above.

At the end of Diet 1, two animals for electron microscopy (EM) and two for histology will be sacrificed from each group. At end of Diet 2, four animals for EM and four for histology will be sacrificed from each group.

Fixation methods will be as previously described.

Sacrificed animals will be decapitated. The specimens will be sent to a histology laboratory where the eyes will be dissected out. This is preferable to immediately dissecting out the eyes as it will minimize handling the eyes until fixed and will help histologists to properly orient the eye on the block.

2. Adjustment of the Dose and the Mode of Administration of Active Compounds Used in the Lens Regeneration 48 3-week old Mongolian Gerbils will be obtained from Charles River Laboratories and divided into the following groups of 6 animals each.

| Group | Regimen | |
|---|---|---|
| 1 | Control | AIN diet |
| 2 | Guanosine | 0.05% in diet |
| 3 | Guanosine | 0.10% in diet |
| 4 | Guanosine | 0.50% in diet |
| 5 | Guanosine | 1.00% in diet |
| 6 | Guanosine | AIN diet; saturated solution of guanosine injected after lentectomy |
| 7 | Guanosine | AIN diet; half-saturated solution of guanosine injected after lentectomy |
| 8 | Guanosine | AIN diet; crystal of guanosine inserted after lentectomy |

Groups 1-5 will enable the investigator to determine whether a much smaller dose than was previously used will be adequate to stimulate lens regeneration. Experimental groups 6-8 will allow to determine whether simply instilling guanosine into the lentectomized eye, rather than providing it in the diet will be adequate to stimulate lens regeneration. These conditions are similar to published regimens for guanidine derivative-mediated transdifferentiation of ventral iris to lens in the newt (Eguchi and Watanabe, *J. Embryol. Exp. Morphol.*, 1973, 30:63-71). The remainder of the protocol (i.e., photoperiod, length of Diet 1, lentectomy, etc.) will be the same as described above (part 1). Diet 2 will always be AIN for this experiment.

3. Standardization of the Lens Regeneration Experiment

The purpose of this experiment is to create a standardized series of stages for future studies.

98 animals will be obtained from Charles River Laboratories and divided into two equal groups.

| GROUP | DIET 1 | DIET 2 |
|---|---|---|
| (1) | Control (AIN) | AIN |
| (2) | Guanosine 1% + Beta-carotene 1% | Beta-carotene 1% |

The animals are fed Diet 1 for 2 weeks and then D for 6 weeks, During Diet I, every 3 days, three animals from each group are sacrificed. During the first 4 weeks of Diet 2, every 3 days, three animals from each group are sacrificed.

During the last 2 weeks of Diet 2, every week, three animals from each group are sacrificed. Other conditions are as described above. Specimens are prepared for histological analysis as previously described.

EXAMPLE 3

Lens Regeneration in Mice and Rats 24 three-week-old strain of REJ mice from Jackson Labs will be obtained. They will be divided into two equal groups.

| GROUP | DIET 1 | DIET 2 |
|---|---|---|
| (1) | Guanosine 1% + Beta-carotene 1% | Beta-carotene 1% |
| (2) | Control AIN diet | AIN |

The temperature will be maintained at 22°C throughout the experiment. The photoperiod will be 12 hours light/dark. The animals will be fed Diet 1 for 2 weeks. Then the animals will be anesthetized with ketamine and xylazine, and then lentectomy will be performed as previously described for gerbils. Then the animals will be fed Diet 2 for 6 weeks. At the end of Diet 1, two animals for EM and two for histology will be sacrificed from each group. At end of Diet 2 four animals for EM and four for histology will be sacrificed.

The same protocol will be repeated with Sprague Dawley rats.

EXAMPLE 4

Stimulating Retinal Regeneration in a Mammal (Gerbil)

Newts and other amphibians are able to regenerate neural retina from retinal pigmented epithelium (RPE) after trauma or experimental retinal detachment (Reyer, pp. 309-390, In: *Handbook of Sensory Physiology VII*, Crescitelli ed. Springer-Verlag, 1977). Even some amphibians which are unable to regenerate lens are able to regenerate retina (Reyer. supra). It is believed that the same protocol which has permitted lens regeneration will also permit retinal (neural retina, photoreceptor) regeneration.

68 five-week-old Mongolian Gerbils will be obtained from Charles River Laboratories and divided into two equal groups.

| GROUP | DIET 1 | DIET 2 |
|---|---|---|
| (1) | Guanosine 1% + Beta-carotene 1% | |
| (2) | Control AIN diet | Control AIN diet |

The preferred source of beta-carotene will be the algae Dunaliela available commercially, e.g., Henkel Coip., La Grange, Ill. As in previous protocols, Diet I will be used for 19 days and Diet 2 for 6 weeks. On day 15, experimental retinal detachments will be made in the right eyes using techniques published for amphibians (e.g. Hasegawa, Embryologia, 1958, 4:1-32; Stone, *J. Exp. Zool.*, 1950, 113:9-32; Keefe, *J. Exp. Zool.*, 1973, 184:185-2061 or mammals (e.g. Mervin et al. *Am J. Ophthalmol.*, 1999, 128:155-164; Chon el al., *Retina.*, 1996, 16:139-44: Takeuchi et al., *Invest. Ophthalmol. Vis. Sci.*, 1995, 36:1298-305), or variations of these techniques.

Four animals will be sacrificed I day after the detachment is created, and then four animals per week for five weeks. At the end of six weeks all remaining animals will be sacrificed. The right eyes will be prepared for histological analysis.

EXAMPLE 5

Axolotl Assay System for Transdifferentiation Agents

A series of transdifferentiation experiments were conducted on Axolotls. These experiments demonstrated the utility of this method as an assay for discovering and comparing transdifferentiation and/or stabilizing agents.

The evidence presented herein showing that copper depletion acts as a transdifferentiation agent in this amphibian skin assay system (as it has conclusively been demonstrated to be a transdifferentiation agent in the rat pancreas to hepatocyte transdifferentiation system) reinforces the statements expressed previously, that (1) transdifferentiation agents tend to be universal in vertebrates, and (2) agents identified in one assay system are likely to work in all vertebrates and in several different organ systems.

This assay method, as described below, has led to the identification of GMP (guanosine 5'-monophosphate), cGMP (guanosine 3',5'-cyclic monophosphate), as well as zinc acetate and inositol as transdifferentiation agents.

Larval Axolotls have an epidermis on a thin basement membrane, under which is a thick collagen layer (green when stained with Gomori trichrome for light microscopy.) Only 3 types of cells are present immediately below and slightly embedded in the collagen layer-(a) fibroblasts, which are generally fusiform and have a characteristic light and ultrastructural appearance, (b) melanophores, which contain numerous round or oval black melanosomes, as well as some premelanosomes, and (c) xanthophores, which, contain organelles known as pterinosomes. These appear as vacuoles in light microscopy and vacuoles with wispy or concentric layered material in electron microscopy. In general, melanosomes are normally found only in melanophores and pterinosomes in xanthophores. Evidence presented by Frost, and reviewed by Bagnara, showed that guanosine acted as a transdifferentiation agent when fed to larval axolotls, causing melanophores to convert o xanthophores as shown by ultrastructural studies.

All Axolotls were 3-5 cm in length at the beginning of the experiment and were obtained from the Indiana University Axolotl Colony, Bloomington, Ind.). They were maintained on beef liver (example A below) or fish pellets (Indiana University Axolotl Colony, Bloomington, Ind.) (examples B and C below).

Temperature was 22°C with a 12 hour light/12 hour dark photoperiod. Water was changed daily before feeding, and when the animals were removed from feeding an hour later. They were fed about every day. Every other day, the experimental substance was sprinkled on the beef or fish pellets. All experimental reagents were obtained from Sigma (St. Louis Mo.). In example A, the animal was kept in a 0.75 quart stainless steel dish with a bottom raised to a plateau in the middle. For feeding, beef liver was placed on the raised bottom partially in and partially out of the water. This permitted the animal to sense the food in the water but prevented the cGMP sprinkled on the beef from washing away. For examples B and C, the animals were kept in individual 280 ml plastic containers that were replaced twice per week. For feeding the animals were transferred to smaller plastic containers (weighing canoes) which have one side sloped. The pellets were placed on the slope, partially in and partially out of the water. This permitted the animal to sense the food in the water but prevented the cGMP sprinkled on the pellet from washing away. Deer Park Spring Water (Breingsville, Pa.) was used exclusively.

The animals were observed about weekly under an Olympus SZ stereomicroscope and most were photographed prior to sacrifice or shortly (hours) after death. Animals were fixed in 10% Formalin and 4 mm punch biopsies of skin were processed routinely for histology (Gomori Trichrome) by Charles River Laboratories (Wilmington, Mass.). Slides were examined in an Olympus (Woodbury, N.Y.) BX40 microscope.

Three animals (a control and two GMP fed animals) were biopsied with a 2 mm punch and fixed in Trump=s fixative for 24 hours, and processed routinely for electron microscopy. They were postfixed in 2% osmium tetroxide, dehydrated in a serials of alcohols and embedded in Epon-Araldite (1:1). Processing and photography were performed at the Electron Imaging Facility, Rutger=s University, Piscataway, N.J.

EXAMPLE A

An Axolotl was fed cGMP by the above method for 22 days and then died. Examination of Gomori trichrome stained skin showed presence of melanosomes and pterinosomes in several cells. This was evidence of the transdifferentiation caused by cGMP of melanophores to xanthophores. The animal was also lighter by inspection. A control animal sacrificed about a week later did not show any cells with both organelles.

EXAMPLE B

Figure 4:
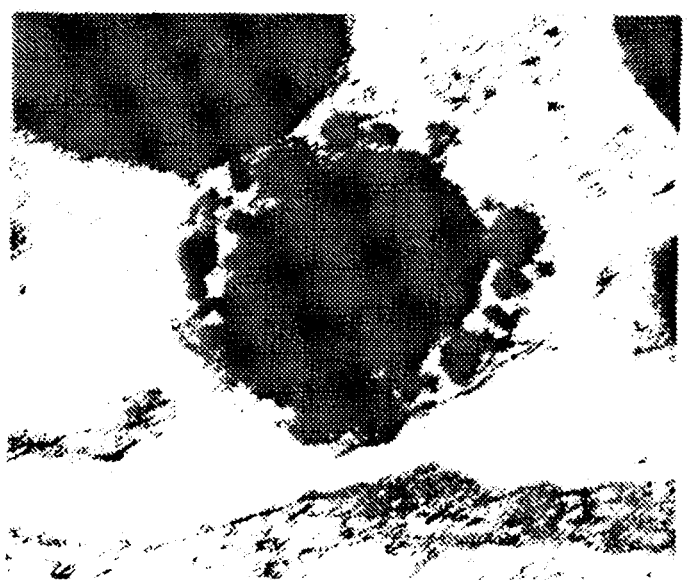
FIG. 4 is a Gomori trichrome stained section of an Axolotl which was fed GMP (described in Example 5B). E=epidermis; C=collagen band in dermis just below basement membrane; M=melanocyte. The two arrows mark the cell which is transdifferentiating from a melanocyte into a xanthophore. The small arrow points to melanosomes. The larger arrow points to a pterinosome, which appears as a white vacuole.

Two Axolotls were fed GMP as described above for 67 days, Electron microscopic examination of one animal=s skin showed many cells in which both melanosomes and pterinosomes were, present (FIG. 1). Some cells showed organelles which appeared to be hybrids of melanosomes and pterinosomes (e.g. the irregular vacuolar structure was similar to that of pterinosomes but there were dark material such as seen in melanosomes (FIGS. 2 and 3). It is believed that such organelles demonstrate transdifferentiation at the organelle level. The second animal showed clear evidence of transdifferentiation by the presence of cells containing both pterinosomes and melanosomes in Gomori trichrome stained light sections (FIG. 4). These animals were also markedly lighter by inspection and had a yellow hue. A control animal also sacrificed on day 67 was in general without cells which had hybrid organelles or cells containing both types of organelles.

EXAMPLE C

Two animals were fed Zinc Acetate as described above. One animal died after 7 days and one animal died after 12 days. A control animal was sacrificed a week after the second zinc fed animal died. Gomori trichrome stained slides revealed cells with both melanosomes and pterinosomes, thus providing evidence that zinc acetate was causing transdifferentiation of melanophores into xanthophores. The control animal, was in general without cells which had hybrid organelles or cells containing both types of organelles.

Similar experiments have been conducted in which the animals have been fed myo-inositol, trien (triethylenetetramine tetrahydrochloride), guanosine, and cytosine. Based on macro observations and photographs of the whole animals, it appears that guanosine (as reported previously by Frost), trien and myo-inositol are agents which transdifferentiate melanophores to xanthophores, while cytosine transdifferentiates xanthophores to melanophores.

EXAMPLE 6

Restoration of Sight in a Dog Blinded by Retinal Degeneration by Stimulation of Retinal Regeneration A dog (male Miniature Schnauzer, 4 calendar years old, weight about 10 kg) was noticed by the owner to be frequently bumping into objects. An experienced veterinary ophthalmologist made the diagnosis of Sudden Acquired Retinal. Degeneration (O=Toole et al., *Veterinary Record,* 1992, 130: 157-161; Miller et al., *J. Vet Res.,* 1998, 59:149-152) after making the following observations on examination: The dog acted completely blind. The pupils were completely dilated. There was no indication of glaucoma, injury or metabolic disease. The dog was started on guanosine (Sigma: St. Louis, Mo.) ½ teaspoon per day (2. 5 gm/day; about 250 mg/kg body weight/day) and Betatene (Henkel, 7.5% Dunaliella beta-carotene) ½ teaspoon per day (2.5 gm/day: about 18.75 mg/kg body weight/day).

Two weeks later examination revealed the dog to be still clinically blind, but the pupils constricted slightly when stimulated with bright focal illumination. The guanosine and Betatene were continued.

Four weeks later the dog was examined again. Pupillary reflexes were similar to those noted in the previous examination. When the ophthalmologist dropped pieces of cotton a few feet in front of the dog, be followed them most of the time as they dropped to the floor. Since the cotton could not be heard, smelled, or felt, it was apparent that the dog could see it.

The cause of SARD is not known, and no predictably successful treatment has been published. Histologically, there is rapid loss of rod and cone outer segments followed by a degeneration of the retinal layers. Different zones of the retina are not equally affected, in contrast to many of the hereditary canine retinal degenerations that have appeared in the literature.

Because of the almost hopeless prognosis of SARD, and the apparent improvement in this dog's vision, the veterinary ophthalmologist concluded that the transdifferentiation protocol described herein above was responsible for demonstrable improvement in vision in this dog. In this example the degeneration of the retina (whatever the ultimate etiology of SARD) served as the destabilizing (dedifferentiating) agent. Guanosine served as the transdiffernetiation agent of RPE into neural retina, and beta-carotene (as Betatene 7.5%) served as the stabilizing agent.

Thus, the methods described led to transdifferentiation of retinal pigment epithelium into neural retina, regenerating the retina, and restoring to a measurable degree, vision to a dog blinded by retinal degeneration.

The dog was examined again 4 weeks later. The owner believed that be could definitely see better in poor lighting than bright lighting. The veterinary ophthalmologist examined him and agreed. When be dropped pieces of cotton in front of the dog, the dog followed the cotton most of time, be did not follow it as frequently in standard exam room lighting as be did in poor lighting.

The veterinary ophthalmologist suggested that the dog continue the oral beta-carotene, but at a higher dose. The veterinary ophthalmologist concluded that the visual function was visibly better than in the previous examination.

EXAMPLE 7

Regeneration of Islet Cells in the Human Pancreas

Islet cells from the human pancreas will be regenerated. A portion of the human pancreas (10 g or more) from an individual will be excised. Cells will be cultured in vitro using culture methods similar to those of Githens et al. (*In Vitro Cell. Dev. Biol.*, 1994, 30A: 622-635). The cells will then be destabilized by the addition of retinoic acid (1-10 μg/ml). Trans-differentiation will be accomplished by the addition of guanosine (1-100 μg/ml). A carotenoid will then be administered as a stabilization agent (1-30 mg/ml in tetrahydrofuran). The resulting islet cells will be proliferated in culture. The islet cells will then be re-implanted into the patients body by injection into the bloodstream or pancreatic blood vessel. The autologous nature of the islet cells will avoid the need for immunosuppression. Preferentially, infants or children under the age of 5, without concurrent diseases will be subjects for this procedure.

EXAMPLE 8

Regeneration of Human Liver Hepatocytes

Hepatocytes will be regenerated from the human pancreas. A portion of the human liver (e.g., 1-100 g) from an individual will be excised. Cells will be cultured in vitro. The cells will then be destabilized by the addition of retinoic acid (1-100 μg/ml). Transdifferentiation will be accomplished by the addition of guanosine (1-100 μg/ml). A carotenoid will then be administered as a stabilization agent (beta-carotene, 1-100 mg/ml). The resulting hepatocytes will be proliferated in culture. The hepatocytes will then be re-implanted into the patients body. The autologous nature of the hepatocytes will avoid the need for immunosuppression. Preferentially, infants or children under the age of 5, without concurrent diseases will be subjects for this procedure.

EXAMPLE 9

Kupffer stem cells of the liver and other macrophages in organs will be cultured in vitro and treated with various agents promoting their transdifferentiation into other cells types such as melanocytes, bone, connective tissue, neurons (Sichel et al., *Pigm. Cell Res.*, 1997, 10:271-289; Labat et al., 2000, supra).

EXAMPLE 10

Transdifferentiation of Neural Crest-Derived Cells

Terminally differentiated cells derived from the neural crest will be induced to transdifferentiate into stem cells or other neural crest-derived terminally differentiated cells by a one- or two-step process. Preferred examples include trans-differentiation of melanocytes or pineal cells to neurons, bone or muscle; cephalic connective tissue to bone, Schwann cells to neurons or bone, etc.

The cells will first be contacted in vitro with a transdifferentiating agent such as guanosine, phenylthiourea, or TPA (1-100 μg/ml). The cells will then be contacted with a differentiating agent such as beta-carotene, retinoids, riboflavin or pteridines (0.1-100 μg/ml).

1. Treatment of Parkinson=s Disease by Transdifferentiation of Melanocytes into Neurons Patients suffering from Parkinson=s Disease will be treated with brain implants of neural cells transdifferentiated in vitro from a patients=own melanocytes. Melanocytes will be harvested and cultured from a biopsy of adult human skin taken from a patient=s hack. Cells will be dedifferentiated by incubation for one week in culture medium containing cyclic guanosine monophosphate (cGMP) at a concentration of 20 μg/ml. At the end of a week the cells will show evidence of de-pigmentation including loss of melanosomes and melanin. The cells will be transdifferentiated and stabilized by incubation in a medium containing basic fibroblast growth factor (30 ng/ml; Sigma. St. Louis, Mo.). After a week, the appearance of neural and glial cells in culture will be confirmed microscopically and/or biochemically and/or immunologically. The neural cells will be then harvested and used for autologous brain implants in Parkinson's Disease patients, using methods documented for embryonic cell implants (Brandin et al., *Brain,* 2000, 123:1380-1390).

2. Treatment of Cataracts by Transdifferentiation of Melanocytes into Lens

Patients suffering from cataracts will have lens cells replaced using transdifferentiated cells grown in culture. Melanocytes will be harvested and cultured from a biopsy of adult human skin taken from a patient=s back. Cells will be dedifferentiated by incubation for one week in copper-depleted culture medium. The cells will be then transdifferentiated into lens cells by incubation for one week in a media containing ascorbic acid 0.2 mM. The appearance of lens cells in culture will be identified by immunological staining for crystallins. The new lens cells will be harvested and used for autologous implants in patients requiring an intraocular lens due to a cataract.

3. Treatment of a Knee Injury by Transdifferentiation of Melanocytes into Cartilage Cells Patients suffering from a knee cartilage injury will have tissue replaced using transdifferentiated cells grown in culture. Melanocytes will be harvested and cultured from a skin biopsy taken from a patient=s arm. Cells will be first dedifferentiated into neural crest stem cells by culturing them in the presence of triethylenetetramine tetrahydrochloride 1-100 μM/l for a week. Cells will be then transdifferentiated into cartilage cells by incubation in a medium containing Transforming Growth Factor Beta (TGF-β; Sigma, St, Louis. MO). The new autologous cartilage tissue will be transplanted into a patient.

4. Transdifferentiation of Melanophores into Iridophores

Melanophores will be induced to transform into Iridophores by a one-step process using massive amounts (30-100 μg/ml) of guanosine in cell culture or by topical application to the skin or by diet.

5. Transdifferentiation of Melanophores into Neurons

Transdifferentiation of melanosome-containing pigmented cells of the central nervous system will enable regeneration of damaged nerves in the central nervous system. Melanosome-containing pigmented cells will be first transdifferentiated into xanthophores using guanosine (1-100 μg/ml) and then into neurons using retinoic acid ($10^{-9}$-$10^{-3}$ M depending on source tissue, culture conditions, and type of neurons desired).

EXAMPLE 11

Treatment of Cancer by Transdifferentiation of Malignant Cells to Benign

Cancer (e.g., melanoma or sarcoma) will be treated in a patient by inducing malignant cells to transdifferentiate into benign terminally differentiated cells by a two-step process. A battery of standard transdifferentiating agents will be screened using cultured cancer cells obtained from a patient, to determine which agent will be the least toxic and the most efficient in converting malignant cells into benign (e.g., melanoma cells into benign xanthophores). In a preferred mode transdifferentiating agents such as guanosine (and other purines), copper depletion agents, phenylthiourea, or TPA, in combination with differentiating agents such as carotenoids (e.g., beta-carotene, canthaxanthin), retinoids, riboflavin or pteridines, will be tested for their ability to transdifferentiate cancer cells and cause growth arrest. The benign phenotype of resulting transdifferentiated cells will be confirmed using biochemical and immunological methods, as well as by assaying mitotic activity, contact inhibition of growth and metastatic ability. Selected transdifferentiating agent(s) will be then applied to the patient=s tumor topically, by injection, or systemically. Since the individual patient's melanoma will be used for in vitro screening, treatment of the tumor will be optimized.

EXAMPLE 12

Induction of Limb Regeneration in Mammals

1. A method to Increase the Regenerative Potential in the Offspring of Mammals

High regenerative ability in newly born mammals (e.g., rodents, rabbits) will be induced by feeding pregnant females high levels (4-1,000 mg/kg) of transdifferentiating and stabilizing agents, such as guanosine and beta-carotene, respectively (4-1,000 mg/kg or 1% of diet for each substance). The offspring is expected to possess large numbers of transdifferentiated or hybrid chromatophores reflecting their increased regenerative ability. The increased regenerative ability of said offspring will be tested using in situ and/or in vitro tissue regeneration assay(s) described in the previous Examples, and compared to the regenerative ability of the offspring derived from pregnant females that were not fed transdifferentiating and stabilizing agents.

2. Regeneration of an Amputated Digit in a Gerbil or Ferret

In gerbils or ferrets that store large amounts of beta-carotene rather than primarily converting it to retinal, an amputated digit will be regenerated by feeding the animal a copper deficiency diet with 1% Dunaliella beta-carotene (Henkel Corp., La Grange, Ill.) for 1 month followed by a copper normal diet with beta-carotene as 2% of their diet for 3 months. A digit (preferentially in an animal without other diseases) will be amputated and regrown within months, 3. Regeneration of an Amputated Digit in a Child A child less then 1.2 years of age (optimally, an infant with no other diseases) who has had a digit amputated will regenerate the lost digit by consuming 4 mg/kg of beta-carotene daily for 3 months. The tip of the digit stump will be surgically opened under local anesthesia first (the trauma functioning as the destabilizing/differentiating agent) and the digit will be kept in a chamber at 35-40☐C all day. Bleeding will be stopped. The digit will regenerate in 6 months, 4. Regeneration of an Amputated Appendage in an Adult An adult (preferably young and without other diseases such as diabetes) with a hand amputated at the wrist will regenerate the missing appendage. Unicellular sebaceous glands of Wolff will be isolated from a biopsy taken from the patient=s palm and cultured in vitro. These are cells in the basal layer of the skin of the palms, soles and eyelids which contain both premelanosomes and sebaceous droplets. (Wolff, Lancet, 1951, 888-889; Pelfin et al., G. It. di Derm., 1970,165:1-5). The cells will be grown to confluency by the addition of a suitable mitogen (such as epidermal growth factor) to the culture medium. Guanosine will be applied topically in an ointment base to the arm stump with an occlusive dressing for 3 months. During these 3 months the patient will be fed 300 mg/day of beta-carotene. Cultured cells will be applied regularly in high density to the wound surface which will be reopened under local anesthesia. The hand will be regenerated.

EXAMPLE 13

A Method for Preventing the Progression of Autoimmune Diseases

The progression of myasthenia gravis (characterized by the presence of antibodies directed against the acetylcholine receptor in the blood that cause damage to the patient's muscles) will be prevented by in vitro transdifferentiation of patient's melanocytes to muscle cells, followed by using these newly generated autologous muscle cells to cleanse patient=s blood of the autoantibodies. The new muscle cells will be first placed in a membrane or mesh which permits blood to enter but retains the cells. These immobilized cells will be then placed in a sterile device similar to a dialysis machine. Once per week the patient will be dialyzed. The harmful antibodies will adhere to the extracorporeal muscle cells and will not be returned to the body. In this way progression of the disease wilt be prevented.

EXAMPLE 14

Treatment of Melanoma by Transdifferentiation of Cells into a Benign Phenotype

Materials and Methods

A human melanoma cell line. G-361, was purchased from the American Type Culture Collection (ATCC catalog number CRL-1424, Manassas, Va.) in a cryopreserved state. Upon receipt, the tube containing the frozen cells was rapidly thawed in a 371C water bath by swirling the bottom ⅓ of the tube for less than 2 minutes. All subsequent steps were conducted using standard methods of sterile technique. The cells were transferred to a T-25 flask containing 5 ml of pre-warmed McCoy=s 5A modified medium (Life Technologies, Rockville, Md.) and incubated at 371 C in a humidified $CO_2$ incubator. After approximately 24 hours, the original medium was removed and replaced with fresh medium and the cells allowed to grow until they reached approximately 70-80% confluency with the medium being replaced every 2-3 days as needed. At this point, the cells were subcultured into Leighton tubes at low cell densities using well known typsin-EDTA subculturing techniques. After subculturing, the cells were allowed to re-establish their growth for 48 hours prior to administration of drugs.

Microscopic observations of the initial human melanoma culture revealed a heterogeneous cell population. Few cells resembled a normal melanocyte phenotype. Very few cells displayed detectable amounts of melanin intracellularly. The majority of the cells appeared to be epithelial in morphology. However, other cell phenotypes were observed in smaller numbers which included fibroblast-type cells, triangular cells and large cells with multiple nuclei. The microscopic phenotypic heterogeneity observed was compatible with karyotypic analysis provided by ATCC showing a heterogeneous population with regards to chromosome number.

Later, beta-carotene in tetrahydrofuran was added to McCoy=s 5A modified medium to a final concentration of about 33 mg/ml with a final concentration of 0.5% THF. This supplemented medium was added to the Leighton tubes after removal of un-supplemented medium and was replaced every 2 days during the 7 clay experimental period. At the end of 7 days, the cultures were fixed in methanol and the cover slips were Giemsa stained.

Results

Beta-carotene exerted a dramatic effect on the human melanoma cell cultures. In comparison with control cultures, a large segment of the starting population died during the experimental period. Of the cells that remained, most had triangular morphology and a large nucleus, consistent with neural cells, or were fusiform in shape, consistent with neuroglial or neurilemmal (Schwann) cells. Extensive, cell death occurred early in the 7 day experimental period and the remaining cells did not seem to divide. There were no mitotic figures observed in the remaining cell population.

Conclusions

It is believed that beta-carotene caused transdifferentiation and stabilization of melanoma cells to morphologically benign neurons and neuroglial/neurilemmal cell phenotypes. Those malignant cells which were not transdifferentiated into a benign phenotype were killed.

EXAMPLE 15

Creation of Stem Cells and Transdifferentiation into Neurons and Neuroglia or Neurilemmal Cells Experiment I Creation of Stem Cells Methods: The melanoma cell line G-361, described in Example 1.4 above was used Guanosine was added to McCoy=s 5A modified medium to a final concentration of 3 mg/ml. This supplemented medium was added to the Leighton tubes after removal of unsupplemented medium and was replaced every 2 days during the 7 day experimental period. At the end of 7 days, the cultures were fixed in methanol and the cover slips were Giemsa stained.

Results: During the 7 day experimental period, guanosine induced phenotypic changes in the overall population such that there were many cells with an increased nuclear to cytoplasmic ratio. There was an increased number of triangular cells consistent with neural phenotypes and cells whose morphology resembled various types of neuroglial. or neurilemmal cells. Many cells exhibiting neuronal morphology were observed with two dendritic Ahorns® on one end of the cells and a long axonal like projection on the other end, By the end of the 7 day experimental period, these cells were frequent in number and readily observed. Some examples of all phenotypes present in the initial culture were also present after the guanosine treatment, at this close level.

Significance: It is believed that guanosine induced the formation of stem cells, and that it furthermore stimulated some of these cells to become neurons and neuroglia or neurilemmal cells, Factors supporting the fact that stem cells were created include: the increased number of cells with a high nucleus to cytoplasm ratio, and, as discussed below, that cells exposed to guanosine and then subsequently to beta-carotene had a somewhat different response, both morphologically and behaviorally, than cells only exposed to beta-carotene (and compared to control melanoma cells).

Experiment II

Transdifferentiation into Neurons and Neuroglia or Neurilemmal

Methods: The melanoma cells line G-361, described in Example 14 above was used Guanosine was added to McCoy=s 5A modified medium to final concentration of 3 mg/ml. This supplemented medium was added to the Leighton tubes after removal of un-supplemented medium and was replaced every 2 days for 7 days. Beta-carotene in THF was added to McCoy=s 5A modified medium at a final concentration of 33 mg/ml with a final concentration of 0.5% THF. This supplemented medium was added to the Leighton tubes after removal of guanosine supplemented medium and was replaced every 2 days for an additional 7 day experimental period. At the end of 14 days, the cultures were fixed in methanol and the cover slips were Giemsa stained.

Results: During the first 7 days, guanosine produced the effects described in Experiment 1 above. However, subsequent beta-carotene treatment did not cause the extensive cell death as occurred with beta-carotene alone in Example 1A above. Rather, more cells survived, and most of those had a neuronal morphology with a large nucleus, triangular cell body, and processes consistent with dendrites and an axon. Close observation revealed that the cellular processes present on the triangular cells. often would be directed towards or touching adjacent cells forming what appeared to be a loose network between the cells resembling neural networks.

Significance: It is believed that guanosine caused transdifferentiation of the melanocytic cells to stem cells. This is supported not only by their morphologic changes, but also that the response of these cells to subsequent beta-carotene, in terms of greater survival, suggests that their phenotype changed. Without wishing to be hound by theory, it is believing that beta-carotene further transdifferentiated the stem cells into neurons and neuroglial and neurilemmal cells, and then stabilized these phenotypes so that these cells established a loose network of interconnecting processes resembling neural networks.

EXAMPLE 16

Transdifferentiation of Normal Melanocytes into Neurons and Neuroglia or Neurilemmal Cells Dupin, et al. (Proc. Nat. Acad. Sri. USA, 2000, 97: 7882-7887) has shown that Endothelian 3 was able to induce the conversion of melanocytes into glial cells. In this Example normal (benign) human melanocytes in culture are obtained from a commercial. supplier (Clonetics, Walkersville, Md.). Methods used in Example 14 above are applied to obtain neurons and neuroglia or neurilemmal cells. The phenotypes of the resulting cells are confirmed by electron microscopy and immunocytochemistry.

EXAMPLE 17

Transdifferentiation of Normal Melanocytes into Autologous Neurons and Neuroglia or Neurilemmal Cells for Autotransplantation Normal melanocytes are isolated from a human skin biopsy using standard methods. The procedures of Example 15 above are applied to produce neurons and neuroglia. Cultures of the resulting cells are put in a pharmacologically appropriate vehicle for injection. The resulting cells are injected into the same individual from which the biopsy is taken. Transplantation is by injection (intraspinal) via lumbar puncture, or intrathecal, or by surgical implantation in nervous tissue. These cells are able to migrate to areas deficient in neurons or neuroglia or Schwann cells, since neural crest derived cells are highly motile. The autologous nature of the cells avoids immunological rejection and any need for immunosuppression by drugs or other means. This method is applicable for treatment of mammals (including humans) with diseases such as Parkinson=s Disease and Alzheimer=s Disease to replace neurons that were destroyed, or in demyelinating diseases such as Multiple Sclerosis, where Schwann cells and neuroglia will be replaced.

EXAMPLE 18

Creating and Regenerating a Developmental Field

I. Steps for Regeneration of a Developmental Field

The universal steps for the regeneration of a developmental field are:

destabilization, transdifferentiation, and stabilization.

When a structure requires regeneration, it is because the structure is either (1) partially or (2) totally removed, (1) In the case of (1) above, the arm is amputated at the elbow, then all elements distal to the elbow (which is in the stump) will have to be regenerated. If the arm is amputated at the wrist. then the entire hand will have to be regenerated.

To regenerate a portion of a developmental field, the stump tissue must be stabilized, e.g., by new trauma or by chemicals. Then transdifferentiation of stump tissues must be accomplished, e.g., by topical or systemic application of copper depletion agents or diets. Finally stabilization is achieved e.g. by topical or systemic application of beta-carotene.

Once the stump tissue is destabilized, the developmental field, by its nature, intrinsically senses the distalness of the level of amputation. It proliferates and then, concomitant with transdifferentiation, provides the missing structures appropriate for every level to restore the complete developmental field (e.g., limb).

(2) in the case of (2) above, the lens of the eye will be used as an example. Complete extraction of the lens leaves no lens material which mieht serve as a stump of like tissue from which the whole lens could be replaced. The structure and its developmental field are entirely lacking. However, the lens developmental field is a component of the eye developmental field. In this situation the eye developmental field. can be considered the "mother" developmental field because its formation precedes the formation of the lens developmental field in time and it gives rise to the lens developmental, field embryologically. The remainder of the eye (and its developmental field) remain intact.

In this situation, the regeneration of the lens developmental field is accomplished by a destabilization, transdifferentiation, and stabilization of tissues from the mother developmental field. Thus the tissues of the iris, which is part of the eye (mother) developmental field, undergo the steps of destabilization, transdifferentiation into lens cells, and stabilization of the lens phenotype.

II. Steps for Creation of a Developmental Field

There are a range of situations in which it is desired to create a developmental field. For instance, if a child is born without an organ or a particular body structure, it would be desirable to create that structure. For instance, some children are born with cerebellar aplasia, which is a lack of the cerebellum of the brain which controls coordination. The developmental field which gives rise to the cerebellum is a component of the brain developmental field. In this case, similar to the case cited above where an entire developmental field must be regenerated, the brain field is the mother developmental field.

The steps for creation of the cerebellar developmental field are similarly destabilization and transdifferentiation and stabilization. In this application, the posterior (back) of the brain would be exposed surgically and a small amount of tissue would be traumatized or exposed to a destabilizing chemical. Then a transdifferentiation inducing chemical agent would be topically applied. Finally a stabilizing agent such as beta carotene would be included in the diet.

This circumstance is different from the regeneration of a complete developmental field cited above, since here the structure never existed in the individual.

Another situation in Which it would be desirable to crate a developmental field is that of creating supernumerary limbs on a mammal. Such structures can be easily induced in lower animals such as amphibians (Goss, 1969). For instance if a ligature is placed around the limb of a newt, a fully formed additional limb which is believed to be functional will sprout at the location of the ligature.

The steps for inducing the formation of it supernumerary structure are destabilization, trans differentiation, and stabilization of tissues of the mother developmental field (e.g. the flank from which the limb extends), or from of the developmental field of the structure itself such as occurs with the newt ligature.

The benefits of functional supernumerary structures such as organs or limbs are obvious—namely providing additional functional capacity to existing natural structures.

EXAMPLE 19

Use of Trauma to Stimulate Destabilization in a Mammal

1. A dog with an inherited retinal degeneration is presented to a veterinarian when the owner notices that it appears to be partially blind. The veterinarian makes a small laser burn of the RPE. This is known to stimulate dedifferentiation and proliferation of RPE cells. Guanosine monophosphate (GMP) is then added to the food at 1 g/kg/day (as a transdifferentiating agent) for a month. When GMP is discontinued, Betatene (Henkel, La Grange, Ill.; 7.5%) is added in the food at 1.3.5 g/day.

2. A dog with a retinal degeneration of unknown etiology is treated with guanosine at 1 g/kg/day for a month (as a destabilizing and transdifferentiation agent for the RPE) as well as with beta-carotene at 1 g/kg/day (as a stabilizing agent). No change is seen in the blindness. The dog is then subjected to a laser burn of the RPE, and the treatment with guanosine and beta-carotene is continued. After one month the guanosine is discontinued. Vision is noted to slowly return after the second month, 3. Alternatively, a 30 gauge needle is introduced just posterior to the limbus to traumatize (and destabilize) the RPE.

4. Alternatively, sodium iodate, a known RPE toxin (*The Retinal Pigment Epithelium, Function and Disease*, Wolfensberger and Marmor eds., 1998, Oxford Univ. Press), is injected iv. at 30 mg/kg. This toxic injury to the RPE causes destabilization of the RPE. and proliferation.

5. To stimulate destabilization of the differentiated state of stump fibroblasts, nerves, schwann cells, and keratinocytes, an amputee has the limb stump surgically opened prior to the use of transdiffereniation and stabilization agents as above.

6. Alternatively, saturated hypertonic saline soaks of the limb stump for twenty minutes, twice per day, for 5 days are performed after the epidermis and collagen scars are derided initially.

What is claimed is:

1. A method for transdifferentiating mammalian cells that have been destabilized by radiation comprising the steps of: (a) contacting the cells with an amount of guanosine monophosphate effective to cause transdifferentiation of said cells; and (b) contacting said cells from step (a) with an amount effective for stabilization of an agent which causes stabilization of cells produced in step a.

2. The method of claim 1, wherein the cells have been exposed to radiation.

3. A method of regenerating stem cells in a subject in need thereof, comprising administering to the subject an amount of guanosine monophosphate effective to cause regeneration of the stem cells.

4. The method of claim 3 wherein the cells are dedifferentiated cells.

5. The method of claim 3, wherein the subject has cancer.

6. The method of claim 3, wherein the subject has been exposed to radiation.

7. The method of claim 3, wherein the stem cells are hematopoietic stem cells.

8. A method of regenerating a developmental field in a subject in need thereof, comprising administering to the subject an amount of guanosine monophosphate effective to cause regeneration of the developmental field in the subject, wherein the developmental field is the hematopoietic system.

9. The method of claim 8, wherein the subject has cancer.

10. The method of claim 8, wherein the subject has been exposed to radiation.

* * * * *